(12) United States Patent
Sato et al.

(10) Patent No.: US 11,690,971 B2
(45) Date of Patent: Jul. 4, 2023

(54) EXACERBATION PREDICTING DEVICE, OXYGEN CONCENTRATING DEVICE, AND EXACERBATION PREDICTING SYSTEM

(71) Applicant: Teijin Pharma Limited, Tokyo (JP)

(72) Inventors: Takayoshi Sato, Tokyo (JP); Sadayoshi Matsumoto, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 374 days.

(21) Appl. No.: 16/613,889

(22) PCT Filed: May 10, 2018

(86) PCT No.: PCT/JP2018/018130
§ 371 (c)(1),
(2) Date: Nov. 15, 2019

(87) PCT Pub. No.: WO2018/212067
PCT Pub. Date: Nov. 22, 2018

(65) Prior Publication Data
US 2020/0139068 A1    May 7, 2020

(30) Foreign Application Priority Data
May 18, 2017 (JP) .................. 2017-099274

(51) Int. Cl.
*A61M 16/20* (2006.01)
*A61M 16/10* (2006.01)
(Continued)

(52) U.S. Cl.
CPC .......... *A61M 16/101* (2014.02); *G16H 50/30* (2018.01); *A61M 2016/0036* (2013.01); *A61M 2205/3334* (2013.01)

(58) Field of Classification Search
CPC ........ A61M 16/101; A61M 2016/0036; A61M 16/0051; A61M 16/024; A61M 16/0069; G16H 50/30
See application file for complete search history.

(56) References Cited

U.S. PATENT DOCUMENTS

2008/0045815 A1*  2/2008  Derchak .............. A61B 5/0205
                                                        600/509
2010/0083968 A1*  4/2010  Wondka ................. G16H 20/40
                                                        128/204.23
(Continued)

FOREIGN PATENT DOCUMENTS

JP    2002-85566 A    3/2002
JP    2005-34341 A    2/2005
(Continued)

OTHER PUBLICATIONS

Ballal et al, A pilot study of the nocturnal respiration rates in COPD patients in the home environment using a non-contact biomotion sensor, Physio. Meas. 35 2513-2527 (Year: 2014).*
(Continued)

*Primary Examiner* — Margaret M Luarca
(74) *Attorney, Agent, or Firm* — Sughrue Mion, PLLC (57) ABSTRACT

Provided is an exacerbation prediction device equipped with a respiration sensing means of continuously sensing respiration data of a patient, a calculation means of calculating stable respiration data that are respiration data during a condition in which a respiratory rate is lowered and stable for a certain period of time from the sensed continuous respiration data of the patient, and a prediction means of predicting occurrence of an acute exacerbation in the patient in accordance with the stable respiration data calculated during a certain period of time.

7 Claims, 5 Drawing Sheets

(51) Int. Cl.
*G16H 50/30* (2018.01)
*A61M 16/00* (2006.01)

(56) References Cited

U.S. PATENT DOCUMENTS

| | | |
|---|---|---|
| 2011/0034819 A1 | 2/2011 | Desforges et al. |
| 2012/0125337 A1 | 5/2012 | Asanoi |
| 2013/0030258 A1* | 1/2013 | Cheung .................. G16H 50/20 600/301 |
| 2013/0245502 A1 | 9/2013 | Lange et al. |
| 2014/0350427 A1 | 11/2014 | Holder |
| 2016/0022951 A1 | 1/2016 | Galbraith |
| 2019/0320930 A1* | 10/2019 | Derkx .................. A61B 5/7203 |

FOREIGN PATENT DOCUMENTS

| | | | |
|---|---|---|---|
| JP | 5916618 B2 | 5/2016 | |
| JP | 2016-137251 A | 8/2016 | |
| WO | 2017032873 A2 | 3/2017 | |

OTHER PUBLICATIONS

Communication, dated Jul. 5, 2021, issued by the China National Intellectual Property Administration in application No. 201880032905.3.

Communication, dated Jan. 13, 2021, issued by the European Patent Office in application No. 18802294.1.

A M Yañez PhD. et al., "Monitoring Breathing Rate at Home Allows Early Identification of COPD Exacerbations", Chest, Dec. 2012, vol. 142, No. 6, pp. 1524-1529, (6 pages total).

International Search Report in International Application No. PCT/JP2018/018130, dated Aug. 14, 2018.

Notice of Reasons for Refusal, dated May 19, 2020, issued by the Japanese Patent Office in Application No. 2019-518735.

* cited by examiner

EXACERBATION PREDICTING DEVICE, OXYGEN CONCENTRATING DEVICE, AND EXACERBATION PREDICTING SYSTEM

TECHNICAL FIELD

The present invention relates to an exacerbation prediction device, oxygen concentration device and an exacerbation prediction system, and especially relates to a configuration that enables advance prediction of acute exacerbation of HOT patients who receive home oxygen therapy mainly for respiratory diseases and prompt support to them, and is capable of providing information that helps a medical staff to diagnose and decide/change a treatment plan in a usual outpatient clinical setting.

BACKGROUND ART

Development of a respiratory gas supply device (hereinafter, also referred to as oxygen concentration device) for obtaining oxygen-enriched gas through separation and concentration of oxygen in air has enabled gradually widespread prescription of oxygen therapy using the oxygen concentration device for various diseases with hypoxemia mainly for patients with respiratory diseases.

Though, in some cases, such an oxygen therapy is provided to a patient hospitalized in a medical institution, when the underlying disease (various diseases with hypoxemia including respiratory diseases, heart disorder) of the patient presents a chronic symptom, and calming and stabilization of the symptom are requires by the oxygen therapy for a long term, performed is a treatment method, wherein the above-mentioned oxygen concentration device is equipped in the home of the patient, and an oxygen-enriched gas supplied by the oxygen concentration device is led around the nasal cavity of the patient using a tube member called cannula, and the patient inhales the gas. This kind of treatment method is referred to as home oxygen therapy or HOT for short.

The above-mentioned home oxygen therapy, since insurance is applied to the therapy in 1985, is prescribed mainly for chronic obstructive pulmonary disease (COPD) and pulmonary tuberculosis sequelae. In Japan, the number of the patients for these diseases is about 260,000 and the number of the patients receiving home oxygen therapy is about 160,000 (as of 2016).

While HOT introduction thus allows patients mainly with respiratory disease a home care, at-home medical information of patients prescribed with HOT (hereinafter, referred to as HOT patient) is hardly grasped at present though the number of HOT patients increases and their medical management becomes an important problem. Conventionally, arterial blood gas and percutaneous arterial oxygen saturation (SpO2) were measured once or twice a month in an outpatient clinic, only with which medical information sufficient for determining the diagnosis and the effect of the treatment of the patient was not obtained.

However, in recent years, a device and a system for counting a respiratory rate are developed, and exacerbation prediction of the HOT patients, including mainly those with respiratory disease, is studied. According to NPL 1, from the observation of 89 patients with COPD for three months on their average respiratory rate in the time zone of (1) 8:00 to 16:00, (2) 16:00 to 24:00, and (3) 24:00 to 8:00, 30 patients who were hospitalized by COPD exacerbation all showed a tendency of increasing the average respiratory rate from five days before hospitalization. Besides, as disclosed in PTL 1 and 2, the system capable of predicting COPD exacerbation based on the monitoring of a mean respiratory rate or a median of respiratory rate is devised.

In NPL 2, Takasaki et al. have examined efficacy of telemedicine for patients with severe chronic obstructive pulmonary disease using a bidirectional transmitter and receiver system equipped with a unidirectional transmitter and receiver system and a picture phone. After obtaining various biological information parameters of the patients hospitalized by acute exacerbation by reading at-home therapy diary, it has been revealed that (1) arterial oxygen saturation (SaO2) has shown a significant decrease from 10 days before hospitalization, (2) increase in the heart rate (HR), increase in the respiratory rate (RR), increase in the body temperature (BT), and change of the body weight (BW) has shown a significant change from about three weeks before hospitalization, respectively.

Furthermore, in NPL 3, Ogawa et al. have examined whether the transition to a ventilatory support by respirator can be predicted from fatigue of the respiratory muscle by performing a respiratory physiology test for patients with chronic respiratory failure. In the results of the examination, it has been revealed that the ratio of tidal volume to vital capacity (VT/VC) and respiratory rate (RR) per one minute each represent a predicted value of the fatigue of respiratory muscle.

CITATION LIST

Patent Literature

[PTL 1] Japanese Unexamined Patent Application Publication No. 2016-137251
[PTL 2] Japanese Patent No. 5916618
[PTL 3] Japanese Unexamined Patent Application Publication No. 2002-85566

Non Patent Literature

[NPL 1] CHEST Original Research "Monitoring Breathing Rate at Home Allows Early Identification of COPD Exacerbations"
[NPL 2] Kozui Kida study group: Pollution-related Health Damage Compensation Association commissioned operation report, 1999 year report "Study on the way of everyday life and health guidance for elderly/severely affected patients" (II-1-(2), study on community care for severe chronic obstructive pulmonary disease of elderly patients by the cooperation with a regional medical association and medical practitioners, P31-P43)
[NPL 3] Kazuhiko Ogawa, Toshihiko Koga (March 1995) "Evaluation of the strength of respiratory muscle in patients with chronic respiratory failure", Journal of Japan Society for Respiratory Care, 4(3), p 164-166

SUMMARY OF INVENTION

Technical Problem

Though, as the above-mentioned known documents each disclose, observation of temporary change of biological information of patients concerning respiratory function such as respiratory rate enables an advance prediction of acute exacerbation for HOT patients including mainly those with respiratory disease, making the prediction for at-home patients might require a heavy financial burden, such as newly installing an instrument at home for measuring respiration of the patient, operating the instrument by the patient and family of the patient, installing a communication means to transmit the measured data or visiting the home of the patient and collecting the data by a person in charge such as clinical test agency, and further day-after-day continuation of analyzing the transmitted/collected data by an analysis person with expert knowledge to judge occurrence possibility of acute exacerbation. In addition, the implementation of the above procedures also requires troublesome operations of the instrument and the data transmission by the patient and family of the patient, which causes a non-negligible problem that made practically the implementation difficult. It has also difficulty in realization from the point of view of the quality of life (QOL) of the patient to always wear the measurement device.

Incidentally, the indices reported so far for a mean and a median respiratory rates may be insufficient, from the point of view of early detection and accuracy, for an index of exacerbation prediction because the effect of elaboration on the respiratory rate during awakening and the effect of the change in the sleep stage (fluctuation of the respiratory rate) on the respiratory rate during sleep are not considered.

Besides, as for the configuration of a conventional oxygen concentration device, though, for example, as shown in PTL 1, an oxygen concentration device equipped with a respiration sensing means embodied by a pressure detecting element to supply an oxygen-concentrated gas in synchronization with the inspiration of the patient is already suggested, the device is not originally configured for enabling continuous observation of the biological information and prediction of occurrence of acute exacerbation, and thus healthcare workers of medical institutions and the like were unable to know the exacerbation prediction quickly.

The present invention is in accordance with the above consideration, and thus aims to enable advance prediction of acute exacerbation of HOT patients, including mainly those with respiratory disease receiving a home therapy, much earlier with higher accuracy and prompt support without causing a financial burden and troublesome operations.

Solution to Problem

In accordance with the present invention, to solve the above-mentioned problem, provided is an exacerbation prediction device comprising: a respiration sensing means of continuously sensing respiration data of a patient, a calculation means of calculating stable respiration data that are respiration data during conditions under which a respiratory rate is lowered and stable for a certain period of time from the sensed continuous respiration data of the patient, and a prediction means of predicting occurrence of an acute exacerbation in the patient in accordance with the stable respiration data calculated during a certain period of time.

In accordance with another aspect of the present invention, provided is an oxygen concentration device comprising: a generation means of generating oxygen-enriched gas by concentrating oxygen in air, an oxygen supply path for supplying generated oxygen to a patient, a respiration sensing means of continuously sensing respiration data of the patient provided in the oxygen supply path, a calculation means of calculating stable respiration data that are respiration data during conditions under which a respiratory rate is lowered and stable for a certain period of time from the sensed continuous respiration data of the patient, and a prediction means of predicting occurrence of an acute exacerbation in the patient in accordance with the stable respiration data calculated during a certain period of time.

In accordance with another aspect of the present invention, provided is an exacerbation prediction system comprising: a patient-side terminal having a respiration sensing means of continuously sensing respiration data of a patient and a transmission means of transmitting all the sensed respiration data of the patient to outside and an external terminal having a calculation means of calculating, after receiving the transmitted respiration data of the patient, stable respiration data that are respiration data during conditions under which a respiratory rate is lowered and stable for a certain period of time from the received continuous respiration data of the patient and a prediction means of predicting occurrence of an acute exacerbation in the patient in accordance with the stable respiration data calculated during a certain period of time.

Advantageous Effects of Invention

The present invention enables advance prediction of acute exacerbation of HOT patients, including mainly those with respiratory disease receiving a home therapy, much earlier with higher accuracy and prompt support without causing a financial burden and troublesome operations.

DESCRIPTION OF EMBODIMENTS

The oxygen concentration device of a preferred example concerning an embodiment of the present invention is explained below with reference to each Fig.

Basic Configuration of the Oxygen Concentration Device Concerning an Embodiment

Figure 1:
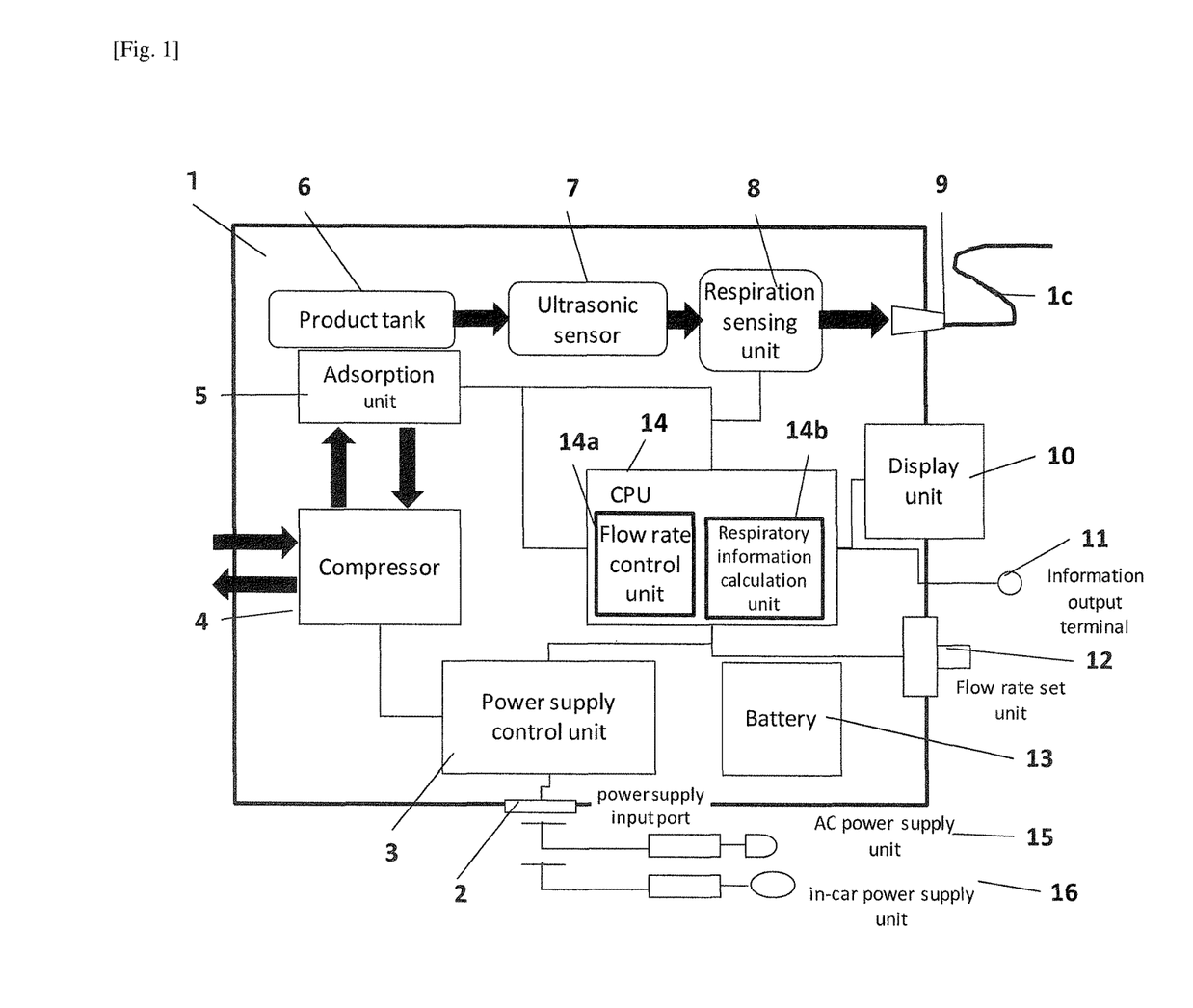
FIG. 1 illustrates a diagram of the configuration of an oxygen concentration device equipped with an exacerbation prediction device concerning an embodiment of the present invention.

FIG. 1 illustrates a diagram of the configuration of an oxygen concentration device equipped with an exacerbation prediction device as a preferred example concerning an embodiment of the present invention. Oxygen concentration device 1 of the present example is a device that separates nitrogen in the air and supplies high concentration oxygen (oxygen-enriched gas) to be used mainly for a home oxygen therapy and is, for example, a pressure swing adsorption type oxygen concentration device, wherein an adsorbent selectively adsorbing nitrogen more than oxygen such as molecular sieve zeolite 5A, 13X or lithium-based zeolite, and the like is filled in an adsorption cylinder (in adsorption unit 5), an air compressed by air compressor (compressor 4) is supplied to the adsorption cylinder, and then an oxygen-enriched gas is taken out. Incidentally, in FIG. 1, the arrow connecting between each block represents a flow of air, and the solid line represents electrical connection between each block.

Compressor 4 is equipped with a compressor drive motor for driving compressor 4, and the compressor drive motor drives and rotates compressor 4 based on a driving current which is generated and output by power supply control unit 3 so that the rotation speed set up by flow control unit 14*a* mentioned later is realized. A compression mechanism unit in compressor 4 is for compressing air using a rotating force obtained by the compressor drive motor, and various types of different compression methods exist for this mechanism and a piston type of reciprocating motion and a scroll type of rotary motion and the like are commonly used, and any type can be used as long as atmospheric air can be compressed.

Power supply control unit 3 has a function to supply driving current output to drive compressor 4 and electric power to each component equipped in device 1.

Besides, when oxygen concentration device 1 of the present example is configured as a portable type as in FIG. 1, it can be considered to adopt a three-way power supply method using a built-in battery, a domestic AC power supply and a DC in-car power supply, by replacing a power supply method using only a domestic AC power supply in the typical conventional oxygen concentration device of fixed installation type. Thus, power supply input port 2 is provided on the housing outer periphery facing the device outside, through which electric power can be supplied from AC power supply unit 15 or in-car power supply unit 16 to be connected to a cigar lighter contact in the car by direct current.

In addition, repeatedly rechargeable battery 13 is removably provided in oxygen concentration device 1, and electric power is supplied to power supply control unit 3 by discharging from battery 13 when power cannot be supplied through the electric power supply input port 2.

Incidentally, charging of battery 13 is usually performed by supplying electric power from AC power supply unit 15 or in-car power supply unit 16 to the battery via power supply input port 2 and power supply control unit 3, while leaving battery 13 incorporated in oxygen concentration device 1.

Oxygen concentration device 1 of the present example, a pressure swing adsorption type oxygen concentration device, as shown in the block diagram of FIG. 1, supplies compressed air obtained by compressing the air by compressor 4, to an adsorption cylinder (provided in adsorption unit 5) filled with an adsorbent adsorbing selectively nitrogen more than oxygen, makes the inside of the adsorption cylinder at a compressed condition and makes nitrogen adsorbed, and then takes out the unabsorbed oxygen. An oxygen enriched-gas, composed mainly of the oxygen taken out from the adsorption cylinder, is accumulated in product tank 6, then supplied to the outside of device 1 from product feed end 9 through sensor unit 7 and respiration sensing unit 8, and is supplied to a user (oxygen therapy patient) through nasal cannula 1*c* which is a tube member for transporting oxygen-enriched gas from oxygen concentration device 1 to around the nasal cavity of the patient.

Incidentally, since the amount of nitrogen an adsorbent can adsorb during one step of adsorption is determined by the amount and type of the adsorbent, before the amount of adsorbed nitrogen on the adsorbent is saturated, a flow path switching valve is switched to open the adsorption cylinder to the atmosphere and decompress the inside of the adsorption cylinder, wherein nitrogen is desorbed and the adsorbent is regenerated. In addition, the flow path switching valve is controlled by main control unit 14 so as to be switched by a duration set beforehand. Incidentally, a vacuum pump can be used to evacuate the adsorption cylinder during the desorption step in order to increase an amount of adsorption/desorption per one step.

Note that, though oxygen concentration device 1 of the present example may be configured for fixed installation at patient home like a conventional oxygen concentration device, in order to realize a smaller and lighter weight device for portable, it is a preferred embodiment to equip adsorption unit 5 provided with a rotation valve means for continuously making a gas flow path in a sequential order of multiple adsorption cylinders for compression and desorption, for example, using the configuration described in Japanese Patent No. 3269626.

Flow rate set unit 12 is operated by a user such as a patient to set a flow rate of an oxygen-enriched gas to be supplied, wherein, when the user operates, for example, a dial switch to select a desired select value from 1 L/m, 2 L/m, 3 L/m, and the like, flow control unit 14*a* senses the selected value and controls operating speed of compressor 4 and adsorption unit 5, and the like to realizes a set desired flow rate. That is, flow control unit 14*a* controls adsorption unit 5 as mentioned above to control the flow rate of the oxygen-enriched gas supplied to the patient while controlling the drive of compressor 4 by controlling power supply control unit 3. In the present embodiment, flow rate control unit 14*a* is recorded in CPU 14.

Sensor unit 7 measures an actual flow rate of an oxygen-enriched gas in a gas flow path. Sensor assembly 7 is, for example, as described in Japanese Unexamined Patent Application Publication No. 2002-214012 and the like, composed of an ultrasonic sensor, which measures propagation velocities of two sound waves, for example ultrasonic waves, propagating in the same and the opposite direction with respect to the direction in which the oxygen-enriched gas flows through nasal cannula 1*c*. Based on the difference of the two measured value, it is possible to determine the actual flow rate of the oxygen enriched gas flowing through nasal cannula 1*c*. Suitable is a configuration in which feedback control based on a measured actual flow rate is performed to modify an operation instruction to compressor 4 and adsorption unit 5 by flow rate control unit 14*a*. Sensor unit 7 may adopt any sensor as long as it can measure an actual flow rate of the oxygen-enriched gas and other configuration and method may be used.

Note that on the implement of the present invention, the configuration concerning a basic oxygen concentration function of oxygen concentration device 1 is not limited to embodiments explained here, and can adopt a well-known configuration or various configurations to be suggested in future.

Exacerbation Prediction Device Concerning an Embodiment

The exacerbation prediction device for a patient concerning the present embodiment is provided with respiration sensing unit 8 and respiratory information calculation unit 14*b* equipped in oxygen concentration device 1. In the present embodiment, respiratory information calculation unit 14*b* is recorded in CPU 14. Flow rate control unit 14*a* and respiratory information calculation unit 14*b* each may have a different CPU.

At a downstream side of sensor unit 7 in the oxygen flow path of oxygen concentrator 1, respiration sensing unit 8 is provided. Respiration sensing unit 8 concerning the present embodiment is, as described in Japanese Unexamined Patent Application Publication No. H7-96035, a respiratory rate measuring device which has a pressure fluctuation sensing means of sensing the pressure fluctuation based on expiration/inspiration and an information processing means of determining a respiratory rate based on sensing information of the sensing means. The information processing means is equipped with an information pre-processing means which is further equipped with a means of digitizing the sensing information consisting of respiration wave forms sensed by the sensing means, and a normalizing means of obtaining a normalized respiration wave form by removing a drift component (a drift component of the sensor signal that is a noise component generated by a shift of signal (pulse count) due to temperature/humidity of the operating environment and long-term use) from a digitized respiration wave form; and a respiratory rate count means of determining a maximum or a minimum value of the processed respiration wave form obtained by the information pre-processing means, determining a detection level by multiplying the maximum or minimum value by a predetermined detection level ratio, and counting a point at which the processed respiration wave form reaches the detection level as a respiratory rate. The information concerning the respiratory rate determined by respiration sensing unit 8 is transmitted to respiratory information calculation unit 14b.

Incidentally, the information processing means of respiration sensing unit 8 may be provided separately from respiratory information calculation unit 14b as mentioned above, or alternatively respiratory information calculation unit 14b may be used as the information processing means. In this case, the pressure fluctuation information acquired by the pressure fluctuation sensing means of respiration sensing unit 8 is transmitted to respiratory information calculation unit 14b, and a respiratory rate is determined based on the information in respiratory information calculation unit 14b. The specific configuration for sensing respiration of a patient in respiration sensing unit 8 is realized not only by the pressure fluctuation sensing means but also by the following, for example, a configuration of converting audio signal (breath sounds of a patient) into a light signal using a light microphone, then into a voltage signal, and further into frequency to perform a frequency analysis in the frequency domain, and sensing respiration by a difference of the frequency band, as a configuration described in Japanese Unexamined Patent Application Publication No. 2002-272845; a method of arranging a sensor unit composed of a pyroelectric sensor to a nasal cannula as described in Japanese Unexamined Patent Application Publication No. S62-270170; a configuration of using a pressure sensor detecting capacitance using a polymer film laminated by a conductive layer as a diaphragm pressure gage described in Japanese Examined Patent Application Publication No. H5-71894; a method of providing a pressure sensor around the oxygen supply port of the oxygen concentration device body to control supply of the oxygen-enriched gas based on the signal of the pressure sensor as described in Japanese Unexamined Patent Application Publication No. H2-88078; or other methods.

Figure 4:
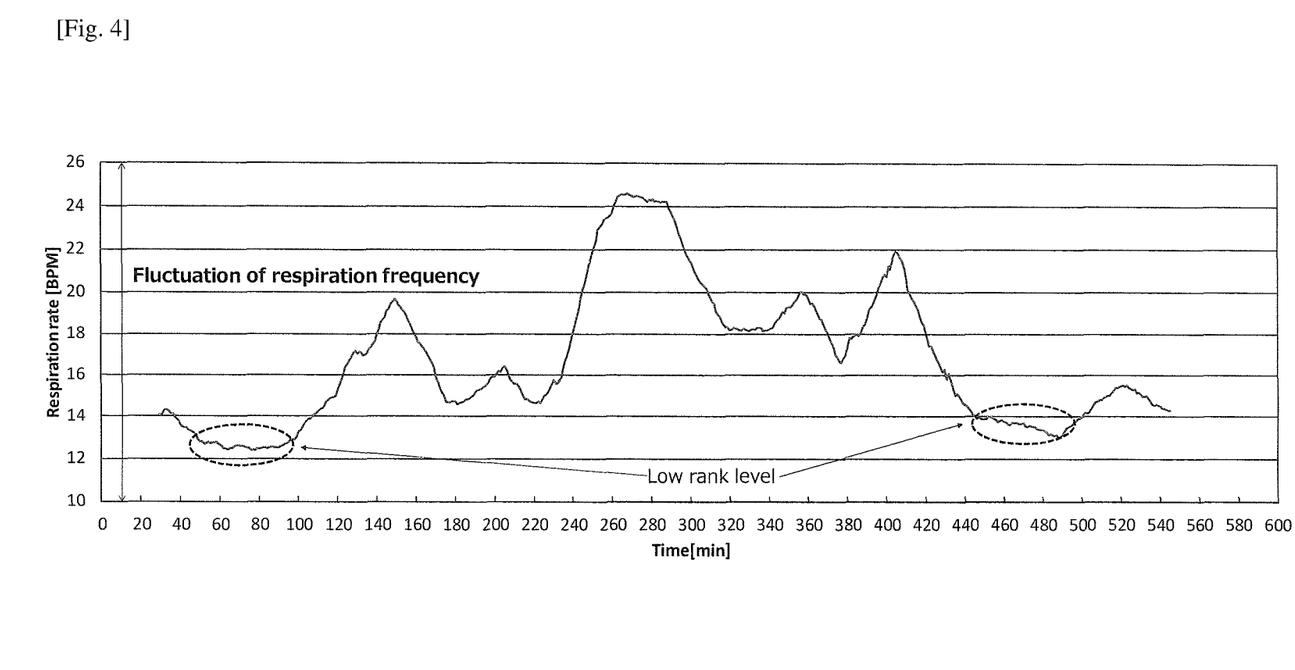
FIG. 4 is a schematic diagram of fluctuation of a respiratory rate.

Respiratory information calculation unit 14b calculates the following indices based on the respiratory rate of the patient acquired as mentioned above. Significance and method of calculating these indices are explained below. The calculated information is transmitted to display unit 10.
(1) Respiratory rate (low rank level) of a patient
(2) Expiration time of a patient
(3) Inspiration time of a patient
(4) Ratio of expiration time and inspiration time of a patient
(5) Prediction result of acute exacerbation occurrence of a patient
Here, as shown in FIG. 4, (1) respiratory rate (low rank level) of a patient is, among all respiratory frequencies (BPM) measured during sleep, an average of all values of respiratory frequencies under the condition in which the respiratory frequency is in the predetermined range (e.g., lower 20%) for a predetermined time (e.g., 20 min or more) and shows a stable state of the fluctuation within a certain range of respiratory rate (e.g., ±3 BPM). In addition, the indices of (2) Expiration time of a patient, (3) Inspiration time of a patient, and (4) Ratio of expiration time and inspiration time of a patient are all for the state in which a respiratory rate is lowered for a certain period of time and is stable.

Incidentally, as for the predetermined range, the predetermined time, and the certain range of respiratory rate, common values for all patients can be set beforehand uniformly, or a healthcare worker can set the values according to medical opinions.

In the present embodiment, oxygen concentration device 1 is configured to be equipped with an interface such as a button and a selector switch, and operation of the above interface by a patient before or after going to bed makes it possible to determine each of the above-mentioned information using the data that are judged as data at asleep state.

Display unit 10 is a display means equipped with a display member such as a liquid crystal panel and a peripheral interface unit, and displays information transmitted from respiratory information calculation unit 14b to the outside of oxygen concentration device 1. The contents of the data displayed in display unit 10 include one or more pieces of information of the above indices (1) to (5) based on the respiratory rate of the patient detected by respiration sensing unit 8 as well as the contents displayed in a conventional oxygen concentration device such as operation state of on, alert and alarm, set flow rate, and the like.

Exacerbation Prediction System Concerning an Embodiment

Figure 2:
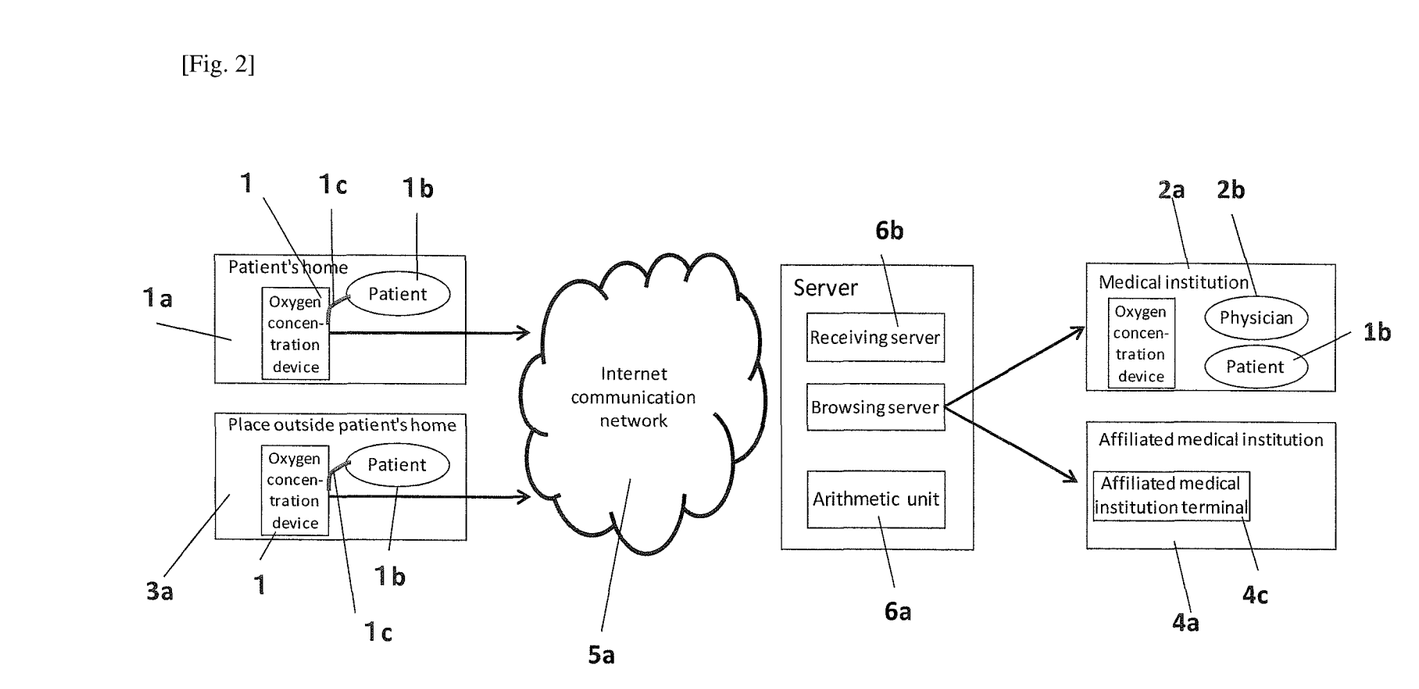
FIG. 2 illustrates a diagram of the configuration of an exacerbation prediction system concerning an embodiment of the present invention.

In the above-mentioned embodiment, the calculation of respiratory rate of the patient and the indices based on the respiratory rate is executed inside oxygen concentration device 1, which alternatively can be done using an arithmetic unit installed outside oxygen concentration device 1. FIG. 2 illustrates a diagram of the configuration of an exacerbation prediction device concerning another embodiment of the present invention.

As show in FIG. 1, oxygen concentration device 1 is equipped with information output terminal 11. Information output terminal 11 is an output terminal or transmission interface for transmitting data calculated in oxygen concentration device 1 to an external device of an oxygen concentration device 1, for example, a personal computer, through a wireless or wired transmission line and may be a configuration according to well-known communication standards such as IrDA, RS-232C, USB, radio communication or others.

Data output from oxygen concentration device 1 through information output terminal 11 to outside are, for example, pressure fluctuation information acquired by a pressure fluctuation sensing means of respiration sensing unit 8 or one or more pieces of information of the above indices (1) to (5) calculated by respiratory information calculation unit 14b.

The data output through information output terminal 11 are transmitted to receiving server 6b in the remote management center and arithmetic unit 6a located in the management center determines information (respiratory rate and/or above-mentioned indices (1) to (5)) based on the respiration data of the patient using the data received and predicts the acute exacerbation of the patient using these pieces of information. A configuration for transmitting various pieces of information such as biological information of the patient, and the like from an oxygen concentration device at home through a transmission line to receiving server 6b in the remote management center is described in detail, for example, in the following bulletins proposed by the present applicants: Japanese Unexamined Patent Application Publication No. H3-143451, Japanese Unexamined Patent Application Publication No. H5-309135, Japanese Unexamined Patent Application Publication No. H6-54910, Japanese Unexamined Patent Application Publication No. H6-233744, and Japanese Unexamined Patent Application Publication No. H7-95963, and the like, and can be realized by quoting appropriately these configurations.

The present embodiment is suitably equipped with a function of transmitting the above-mentioned information and prediction result based on the respiration data of the patient from the management center to oxygen concentration device 1, and displaying them on display unit 10 or outputting from information output terminal 11. Furthermore, the above-mentioned information and prediction result based on the respiration data of the patient can be stored after calculation in a storing means (not illustrated in the Fig.) in arithmetic unit 6a and be output to display and so on when necessary. Adoption of such a configuration makes oxygen concentration device 1 configured simpler and thus reduce cost. The adoption enables a person in charge of the management center, a healthcare worker of a medical institution, and the like to know the exacerbation prediction quickly and thus further provides a merit of a quick support of contacting and visiting the patient's home. In a usual outpatient clinical setting also, it helps a medical staff to diagnose and decide/change a treatment plan.

Method for Predicting Occurrence of Acute Exacerbation

Explained below is a principle, which was found by the inventors of the present application, of predicting occurrence of the acute exacerbation of the HOT patients including mainly those with respiratory disease.

As mentioned above, in recent years, a device and a system for counting a respiratory rate are developed, and exacerbation prediction of the HOT patients, including mainly those with respiratory disease, is studied. However, the conventionally known respiration data used for grasping the sign of acute exacerbation of respiratory disease were an average and a median value of all measured data or an instantaneous value. That is, the above is thought to be under either of the following conditions: monitoring instantaneously increased or decreased values due to change of "oxygen demand from tissues" and "oxygen supply capacity of heart and lungs" during awakening and during sleep, which is described below, or monitoring an average and median values calculated from values including the above-mentioned increased or decreased values.

Inventors of the present application have engaged for many years in the popularization of a home therapy particularly a home oxygen therapy, and had the opportunity to obtain various and useful information and instruction from the patients receiving the therapy and healthcare workers engaging in the therapy using the oxygen concentrator. After considering the various information obtained, inventors of the present application obtained the findings such as the following (1) and (2) which enable prediction of the acute exacerbation much earlier with high accuracy.

Figure 3:
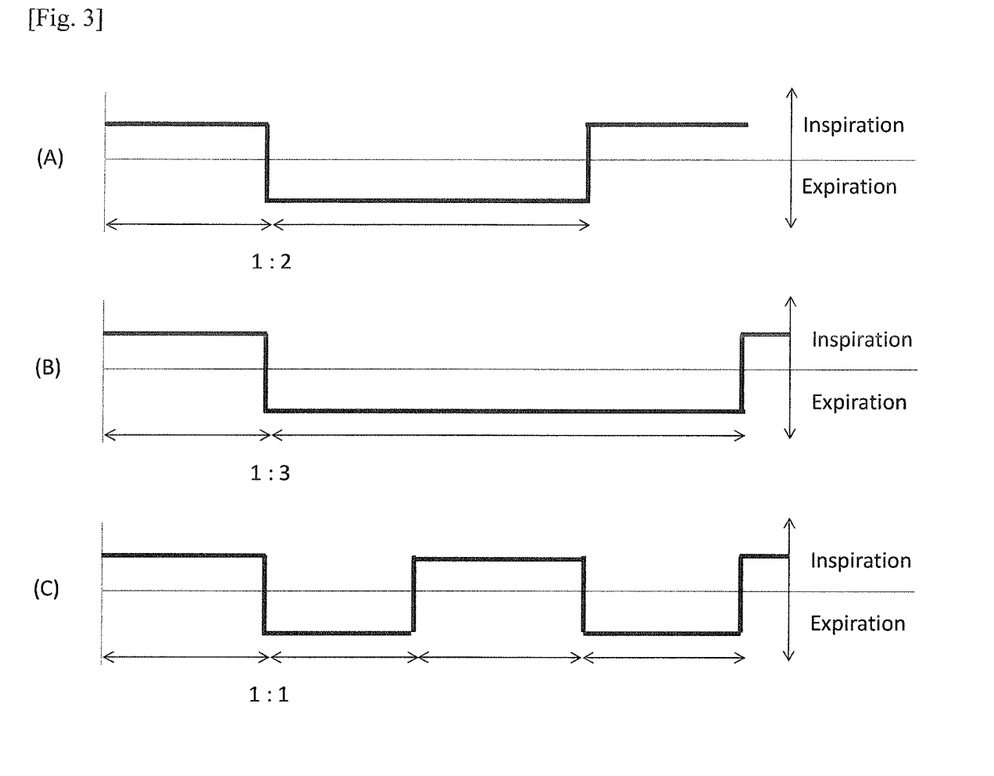
FIG. 3 is a schematic diagram of expiration inspiration ratio.

(1) As shown in FIG. 3 of a schematic diagram of expiration-inspiration ratio, at first as for exhalation-inspiration ratio of a healthy subject, the ratio of inspiration, i.e., time for inspiring air, to expiration, i.e., time for expiring air, is about 1:2 as shown in (A) of the Fig. On the other hand, the expiration time tends to be prolonged for a COPD patient. (B) of the fig. illustrates the case where expiration time is prolonged to the ratio of 1:3. This is caused by the following reason: in the case of many COPD patients, since the airway is obstructed to limit the flow of air, though air is easily flown into the lungs at the inspiration because the chest can be spread, when air is expired, air must be expired through the narrowed airway, wherein it takes time before all is expired. As for COPD patients at an advanced stage, on the contrary, the expiration time tends to be shortened. (C) of the Fig. illustrates the case where the expiration time is shortened to the ratio of 1:1. Such shortened expiration time at the advanced stage is assumed to be caused by the following reason: at the advanced stage, since the airway becomes more narrowed due to infection and the like and thus the amount of ventilation decreases, which works to increase the respiratory rate, i.e., the number of inspirations per unit time, to improve even a little amount of ventilation per unit time.

(2) Respiration is performed to satisfy the oxygen demand of tissues and organs, and is thought to consist of voluntary respiration and involuntary respiration. The voluntary respiration is conscious respiration that, in many cases during awakening and under the voluntary control from the motor area in the precentral gyrus of the cerebral cortex, can be controlled freely the speed and depth of the respiration within a certain range. On the other hand, when voluntary control is lost, e.g., during sleep, though rhythmical contraction of respiratory muscles persists, respiration is performed unconsciously. The above respiration is involuntary respiration, is controlled by the brainstem, mainly the respiratory center in the medulla oblongata, and is said to be usually under the condition in which the respiratory frequency is not stable (condition with a fluctuating respiratory frequency) (FIG. 4). The human respiratory frequency is determined by various factors, and can be explained using, as one factor, a balance between two elements of "oxygen demand of tissues" and "oxygen supply capacity of heart and lungs". Since the respiratory frequency is thought to be determined by the oxygen demand of the tissues and cardiopulmonary oxygen supply capacity of the heart and the lungs of each person, the condition under which the respiratory rate is lowered and stable for a certain period of time is assumed to be a condition under which "oxygen demand of tissues" is constant and the oxygen demand of the tissues is low. When "oxygen demand of tissues" is increased under the condition of lowered respiratory rate, the compensatory mechanism to the heart and the lungs works immediately to increase the respiratory rate, and thus the condition of being stable for a certain period of time does not appear. On the other hand, as for a time zone of increased respiratory frequency (high rank level) among respiratory frequencies during nocturnal sleep, it is judged that fluctuations of both "oxygen demand of tissues" and "oxygen supply capacity of heart and lungs" increase the respiratory frequency. That is, under the condition of lowered and stable respiratory rate during sleep, in which "oxygen demand of tissues" is thought to be low and stable, it is judged that the lowered "oxygen supply capacity of heart and lungs" can be grasped more conspicuously in the form of increased respiratory rate as an exacerbation sign of diseases including respiratory disease such as COPD and the like. From the above consideration, a monitoring index for predicting much earlier with high accuracy the exacerbation sign of COPD and the like can be judged as a condition under which the respiratory rate is lowered and stable for a certain period of time. Monitoring and observation, for a certain period of time (daily or monthly), of the value of respiratory rate under the condition in which the respiratory rate is lowered (low rank level) and stable for a certain period of time during nocturnal sleep is thought to enable prediction, earlier than a conventional method, with high accuracy, for the acute exacerbation of HOT patients including mainly those with respiratory disease receiving therapy at home. On the other hand, during awakening, activities such as conversation and diet, elaboration, room-to-room movement, going to toilet, bathing and the like are performed, and thus frequent and much times of "oxygen demand of tissues" are present compared with sleep time. Thus, this is difficult to be separated from a change of "oxygen supply capacity of heart and lungs" because both are present in a complicatedly mixed state. During awakening, grasping of the time zone when only "oxygen supply capacity of heart and lungs" changes under the condition of constant "oxygen demand of tissues" can be obtained by grasping the time zone of body motion using a device equipped with an acceleration sensor capable of acquiring various information such as inclination and movement, vibration and shock and by making the load given to a patient constant.

Based on the above-mentioned findings (1) and (2), inventors of the present application have found that detection of the occurrence of at least any one of the following conditions enables to know that the patient is now at an advanced stage, that is, to predict beforehand an acute exacerbation of the patient, and reached the present invention, the conditions are as follows: increase in the respiratory rate per unit time (high rank level, average value, low rank level), change in the ratio of inspiration time and expiration time in the direction of shortening the expiration time under the condition in which the respiratory rate is lowered and stable, and reduction of expiration time. In addition, the respiration pressure pattern under the condition in which the respiratory rate of a patient is lowered and stable, particularly the respiration pressure pattern at an advanced stage, exhibits a pressure pattern with a characteristic inherent in each patient. Therefore, continued monitoring of the current respiration pressure pattern based on the prior knowledge of the respiration pressure pattern at an advanced stage of a certain patient enables to know that the patient is at an advanced stage by detecting that a respiration pressure pattern has approached to the pressure pattern at the advanced stage, and the acute exacerbation of the patient can be predicted beforehand in the same way as above.

Operation of Exacerbation Prediction Device or Exacerbation Prediction System

Next, the operation of the exacerbation prediction device or the exacerbation prediction system of the present example is explained mainly on the operation of predicting occurrence of acute exacerbation of a patient. Referred to as necessary are a connection diagram of device 1 shown in FIG. 2, a schematic diagram of the expiration-inspiration ratio shown in FIG. 3, and a schematic diagram of fluctuation of a respiratory rate shown in FIG. 4. Respiratory information calculation unit 14*b* of the exacerbation prediction device or arithmetic unit 6*a* of the exacerbation prediction system of the present example is configured to predict beforehand an acute exacerbation of the patient based on the above-mentioned findings of the inventors of the present application, and thus at first acquired is at least any one of the following pieces of information based on the data of respiration of the patient sensed by respiration sensing unit 8 under the condition in which the patient is using oxygen concentration device 1. Then, these respiration data acquired daily are monitored over time and trend data over multiple days (e.g., from several days to several months) are stored.

(1) Respiratory rate (low rank level) of a patient
(2) Expiration time of a patient
(3) Inspiration time of a patient
(4) Ratio of expiration time and inspiration time of a patient Then, respiratory information calculation unit 14*b* or arithmetic unit 6*a* compares a value and a gradient of the recorded trend data at an arbitrary point of time with predetermined thresholds concerning the magnitude, determines whether the value and the gradient of the acquired information are within the predetermined range or not, and judges the patient as at advanced stage if the data are within the range. The above-mentioned predetermined range is a range predetermined by the above-mentioned threshold so that if a value of the acquired information is out of the range, the patient is judged as at the advanced stage.

AS for the above-mentioned threshold, a value common to all patients may be set beforehand uniformly, a healthcare worker may set the value according to medical opinions, or a value generated automatically by respiratory information calculation unit 14*b* or arithmetic unit 6*a* from the respiration data of the patient acquired by respiration sensing unit 8 of oxygen concentration device 1 may be used under the careful examination by the healthcare worker. When multiple indices are acquired, respiratory information calculation unit 14*b* or arithmetic unit 6*a* judges whether the patient is at advanced stage by using the judgment after comparing the value(s) of either one or more indices with the corresponding threshold(s), or combining the judgement with evaluation results of various other parameters, for example, by measuring percutaneous arterial oxygen saturation (SpO2) over multiple days at the same timing as the above respiration data and considering the relationship with the respiration data.

As a result of the judgment, when acute exacerbation is predicted, respiratory information calculation unit 14*b* or arithmetic unit 6*a* transmits the judgement result to display unit 10. When receiving a judgment that acute exacerbation is predicted, display unit 10 displays a warning message such as "Respiratory rate has increased. Notification to the medical institution is recommended." Also, a signal implying the same contents is output from information output terminal 11, which may allow an external display means to display and an external printer to indicate.

Alternatively, in the case where acute exacerbation is predicted, it may be configured so that the signal informing of the case is delivered via information output terminal 11 to a terminal in the management center, a terminal of the medical institution, a mobile phone of a healthcare worker or family of the patient, and the like.

Separately from or in parallel with the above-mentioned judgment by magnitude comparison between a predetermined threshold and measurement data, it may be configured so that a correlation coefficient is calculated to make judgement.

The judgment using the correlation coefficient is a method perforated as follows: acquiring beforehand a respiration pressure pattern of the patient at normal time and/or at exacerbation time, and comparing a current respiration pressure pattern of the patient with the acquired patterns based on the well-known technique of pattern matching to know whether the current respiration pressure pattern of the patient is close to the respiration pressure pattern at normal time or the respiration pressure pattern at exacerbation time, or to know which of the two patterns the current pattern is closer to.

Method for Operating Oxygen Concentration Device Equipped with Exacerbation Prediction Device or Exacerbation Prediction System Explained below is a procedure of displaying and outputting of respiration data at a visited hospital as well as general operation of oxygen concentration device 1 of the present example with reference to FIG. 2.

When patient 1b receives oxygen therapy at the patient's home 1a, the patient, as usual, can inhale oxygen-enriched gas from oxygen concentration device 1 of the present example by receiving electric power from a domestic AC power supply. Further, when inhalation is performed via a device driven by battery 13 at the patient's home, patient 1b can continue the inhalation by carrying device 1 with him/her while freely moving around the patient's home without being constrained by the AC outlet. Accordingly, dissolved is inconvenience, as in a conventional fixed installation type device, of connecting a cannula with a long and bulky extension tube of several meters to an oxygen concentration device and inhaling via the cannula equipped with this extension tube.

As for a characteristic feature of the present example, while oxygen-enriched gas is supplied, arithmetic unit 6a calculates, always or at an appropriate timing, the above-mentioned information on the respiration data of the patient and records/store the information in the memory unit (not illustrated in the Fig.) in CPU 14.

A medium for recording/storing the above-mentioned information may be, instead of a memory in CPU 14, a memory means provided independently or a removable memory means. At the visit to medical institution 2a, a removable memory means alone may be taken out and brought to medical institution 2a, instead of bringing whole the oxygen concentration device 1. Alternatively, as for a method for delivering the above-mentioned information on the respiratory pattern to an information appliance of the medical institution, although the patient brings oxygen concentration device 1 to medical institution 2a for visiting, the information is delivered by so-called medium delivery: removing the removable memory means from oxygen concentration device 1 and then attaching it to an information appliance of the medical institution.

The information on the respiratory pattern may be generated not only at patient home 1a but also, of course, at a place outside the patient's home 3a.

Then, patient 1b visits the medical institution carrying oxygen concentration device 1 regularly, e.g., on a monthly visit day. Physician 2b of medical institution 2a confirms the data by making display unit 10 of device 1 display respiration data such as those mentioned above or data having other configuration, or displays the data on a personal computer connected to information output terminal 11 through transmission cable 2e or other transmission path, and confirms the data. These procedures help a healthcare worker to grasp the condition of the patient and can greatly promote treatment effect of the home oxygen therapy.

Of course, it is possible to adopt a configuration of printing respiration data on a paper medium using a print means, which is not illustrated.

In addition, the information on the respiratory pattern output at the medical institution at visit may be transmitted to affiliated medical institution terminal 4c of affiliated medical institution 4a, which offers the patient medical care in collaboration with medical institution 2a, under security management via Internet communications network 5a, to share the medical information.

Exacerbation Prediction by Combination of Respiratory Rate Information and Other Information HOT patients, including mainly those with respiratory disease, are reported to present desaturation, lowered SpO2 level, during nocturnal sleep. Desaturation during sleep is known to lead to sleep disruption by waking reaction, pulmonary hypertension and poor prognosis. Until now, most of the medical information of HOT patients, including mainly those with respiratory disease, was not grasped. Conventionally, although arterial blood gas and percutaneous arterial oxygen saturation (SpO2) were measured once or twice a month in an outpatient clinic, these data alone did not yield sufficient medical information for determining the diagnosis and the effect of the treatment of the patient.

Decrease in the percutaneous arterial oxygen saturation (SpO2) at nocturnal sleep of HOT patients, including mainly those with respiratory disease, is combined with respiratory information to enable grasping and predicting of the pathophysiology, and makes it possible to provide information for treatment corresponding to the pathologic condition at an appropriate timing.

Figure 5:
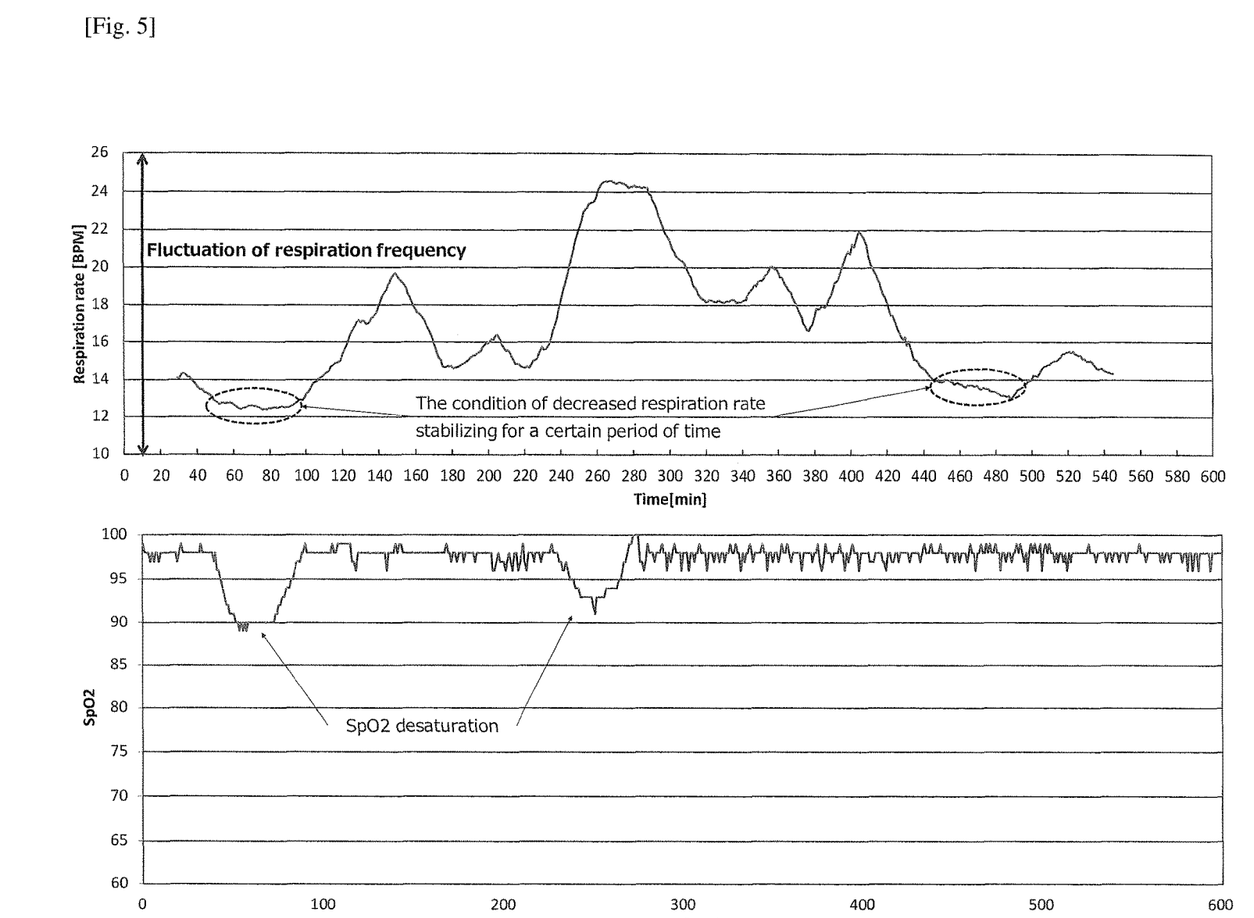
FIG. 5 is a diagram showing the waveforms of a respiratory rate and SpO2 measured simultaneously.

Respiratory rate is said to present a condition of unstable respiration (with fluctuation) during sleep as shown in FIG. 5, and simultaneous observations of fluctuation of respiration (frequency) and a change of SpO2 at night enable distinction between a situation of physiologically uneventful respiration change and a situation in which a cardiorespiratory function cannot respond to the oxygen demand. For example, in the case where, when SpO2 level is decreased at nocturnal sleep, the respiratory rate is lowered and stable for a certain period of time, the case is judged as a situation in which a cardiorespiratory function cannot respond to the oxygen demand. As for this, human respiratory frequency is determined by various factors, and can be explained using, as one factor, a balance between two elements of "oxygen demand of tissues" and "oxygen supply capacity of heart and lungs". The respiratory frequency is thought to be determined by the oxygen demand of the tissues and the cardiopulmonary oxygen supply capacity of each person, and thus in the case where SpO2 decreases, that is, "oxygen demand of tissues" becomes higher, the condition under which the respiratory rate is stable for a certain period of time is judged not to appear since the compensation mechanism to the heart and lungs immediately works to increase the respiratory rate. The condition under which the respiratory rate is stable for a certain period of time in this case is an abnormal condition under which "oxygen supply capacity of heart and lungs" does not respond. The decrease in SpO2 as above is combined with the respiratory information to enable the classification of the desaturation degree and the supply of information for treatment at an appropriate timing corresponding to the pathologic condition. AS for the respiratory information, I/E ratio, intensity of respiration, gradient (change thereby) of inspiration and expiration obtained from I/E ratio and respiration time as well as a respiratory rate can be used for confirmation.

In addition, the respiratory information is combined with SpO2 level to determine the desaturation degree, and the feedback of it to a therapy device such as an oxygen concentration device enables the control of parameters for the treatment (e.g., flow rate and oxygen concentration of an oxygen concentrator for home oxygen therapy).

REFERENCE SIGNS LIST

1. Oxygen concentration device
3. Power supply control unit

4. Compressor
5. Adsorption unit
8. Respiration sensing unit
14. Main control unit
6A. Arithmetic unit

The invention claimed is:

1. An exacerbation prediction device comprising:
a respiration sensor configured to continuously sense respiration data of a patient; and
a processor configured to:
calculate stable respiration data, based on respiration data that are sensed during a sleep of the patient, by determining the stable respiration data as a portion of the respiration data that satisfies a condition in which a respiratory rate of the respiration data is lowered and stable for a certain period of time among the respiration data of the patient that is sensed during the sleep of the patient among the continuously sensed respiration data, and
predict an occurrence of an acute exacerbation in the patient based on the stable respiration data calculated with respect to the certain period of time.

2. The exacerbation prediction device according to claim 1, wherein the stable respiration data are at least any one of (a) a respiratory rate of the patient, (b) a ratio of an expiration time and an inspiration time of the patient, and (c) the inspiration time of the patient, during the certain period of time during the sleep of the patient in which the condition in which the respiratory rate is lowered and stable is satisfied.

3. The exacerbation prediction device according to claim 1, wherein the stable respiration data are at least one from among (a) a correlation coefficient between a current respiration pressure pattern of the patient and a predetermined respiration pressure pattern that is predetermined for the patient and (b) a correlation coefficient between a current respiration pressure pattern of the patient and a predetermined respiration pressure pattern at acute exacerbation time, during the certain period of time during the sleep of the patient in which the condition in which the respiratory rate is lowered and stable is satisfied.

4. The exacerbation prediction device according to claim 1,
wherein predicting the occurrence of the acute exacerbation in the patient comprises determining whether the stable respiration data indicates at least one predetermined ratio between an inspiration time and an expiration time of the patient during the certain period.

5. The exacerbation prediction device according to claim 1,
wherein determining the stable respiration data as the portion of the respiration data that satisfies the condition comprises determining the portion to be lowered and stable for the certain period of time as compared to at least one other portion of the respiration data of the patient that is sensed during the sleep of the patient.

6. An oxygen concentration device comprising:
a compressor configured to compress an air;
an adsorption cylinder configured to receive the compressed air from the compressor, selectively adsorb nitrogen from the air, and output an oxygen-enriched gas;
an oxygen supply path configured to supply the oxygen-enriched gas to a patient;
a respiration sensor provided in the oxygen supply path and configured to continuously sense respiration data of the patient; and
a processor configured to:
calculate stable respiration data, based on respiration data that are sensed during a sleep of the patient, by determining the stable respiration data as a portion of the respiration data that satisfies a condition in which a respiratory rate of the respiration data is lowered and stable for a certain period of time among the respiration data of the patient that is sensed during the sleep of the patient among the continuously sensed respiration data, and
predict occurrence of an acute exacerbation in the patient based on the stable respiration data calculated with respect to the certain period of time.

7. An exacerbation prediction device comprising:
a patient-side terminal having a respiration sensor configured to continuously sense respiration data of a patient, and an output terminal configured to transmit the continuously sensed respiration data of the patient to an outside, and
an external terminal having a processor configured to:
receive the continuously sensed respiration data of the patient,
calculate stable respiration data based on respiration data that are sensed during a sleep of the patient, by determining the stable respiration data as a portion of the respiration data that satisfies a condition in which a respiratory rate of the respiration data is lowered and stable for a certain period of time among the respiration data of the patient that is sensed during the sleep of the patient among the continuously sensed respiration data, and
predict an occurrence of an acute exacerbation in the patient based on the stable respiration data calculated with respect to the certain period of time.

* * * * *